United States Patent [19]

Suthanthiran et al.

[11] Patent Number: 4,946,435
[45] Date of Patent: Aug. 7, 1990

[54] FLEXIBLE SEALED RADIOACTIVE FILM FOR RADIOTHERAPY, AND METHOD OF MAKING SAME

[75] Inventors: Krishnan Suthanthiran, Lorton, Va.; Raj Lakshman, Bethesda, Md.

[73] Assignee: Best Industries, Inc., Springfield, Va.

[21] Appl. No.: 261,327

[22] Filed: Oct. 24, 1988

[51] Int. Cl.⁵ .............................................. A61N 5/00
[52] U.S. Cl. .......................................... 600/3; 600/1
[58] Field of Search .......................... 600/1, 3, 6, 7, 8

[56] References Cited

U.S. PATENT DOCUMENTS

| | | |
|---|---|---|
| 2,269,027 | 1/1942 | Klinghoffer ............................ 600/1 |
| 3,189,581 | 6/1965 | Hart et al. . |
| 3,218,357 | 11/1965 | Roelen et al. . |
| 3,325,459 | 6/1967 | Gander . |
| 4,112,213 | 9/1978 | Waldman . |
| 4,674,480 | 6/1987 | Lemelson . |

FOREIGN PATENT DOCUMENTS 0381407 10/1932 United Kingdom .................... 600/1

*Primary Examiner*—Alan W. Cannon
*Attorney, Agent, or Firm*—Arnold, White & Durkee

[57] ABSTRACT

A flexible sealed radioactive film for medical treatments comprising a radioactive material on or in a flexible substantially two-dimensional film and sealed in a substantially two-dimensional envelope. A number of flexible sealed radioactive film units can be provided in the form of a perforated strip wherein any number of flexible sealed film units can be easily removed from the perforated strip and applied to the site of treatment. The flexible sealed radioactive film can be easily applied to irregular contours to provide radiation treatment for diseased tissue and the like. Methods of making the flexible sealed radioactive film are also disclosed.

37 Claims, 2 Drawing Sheets

FLEXIBLE SEALED RADIOACTIVE FILM FOR RADIOTHERAPY, AND METHOD OF MAKING SAME

BACKGROUND

The present invention relates to a flexible sealed radioactive film useful for medical treatments and a method for producing such radioactive films.

Radioactive materials have been used in the medical treatment of diseased tissues. Such radioactive materials may be implanted into a patient at the site of the diseased tissue. It is desirable to have the radioactive material in a form which will permit it to be used to irradiate the diseased tissue while minimizing damage to nearby healthy tissue. Therefore, it is desirable to have a source which will uniformly irradiate an area being treated with a controlled desired dosage of radiation. Also desirable is a method of easily applying such sources to the area being treated.

Radioactive iodine sources have been used in radiation therapy in the form of a radioactive seed which is implanted into the patient at the site being treated. Such methods of radiation treatment provide radiation patterns in a circumferential area around the whole seed. Although such seeds provide adequate treatment for some diseased tissues, they are unable to provide adequate radiation for areas of the body which require more specific or irregular radiation patterns, such as the treatment of diseased eye tissue. Further, such seeds are difficult to place and retain in the desired area for treatment of residual tumor cells remaining on the walls of cavities resulting from surgical removal of a tumor from the body. Such residual tumor cells cannot be adequately treated by radioactive seeds.

Another method of treating diseased tissue is disclosed in Lemelson U.S. Pat. No. 4,674,480 in which fluid disposed within a container or capsule implanted in the diseased tissue is released to infiltrate the surrounding tissue. The fluid is rendered explosively radioactive when targeted within a living body by external radiation passed through the body to the container or capsule containing the radioactive fluid. This method has the disadvantage in that the fluid may infiltrate healthy tissue and other areas where radiation is not desired.

It is desirable to provide sources of radiation which can be readily adapted for application to the site of therapy and from which the amount of radiation to the site can be readily controlled. However, it will be appreciated that the prior art fails to disclose a truly convenient, advantageous and safe method for providing radioactive materials which provide maximum irradiation at an area of treatment while being easily applied to the treatment site. Also, the prior art fails to disclose a method for easily manufacturing large numbers of such radioactive sources.

SUMMARY OF THE INVENTION

Accordingly, it is an object of the present invention to provide a new and useful flexible sealed radioactive film for radiation therapy, which sealed film overcomes the shortcomings of the prior art.

It is an object of the present invention to provide a radioactive strip, a length of which is capable of providing controlled, uniform distribution of radioactivity in a treatment site.

It is an object of the present invention to provide a flexible sealed radioactive film which can be readily and easily applied to a treatment site.

It is yet another object of the present invention to provide a flexible sealed radioactive film which is readily adaptable to fit the contours of irregular areas of diseased tissue and which can be shaped and controlled to provide an effective radiation pattern to the diseased tissue while nearby healthy tissue remains substantially unaffected.

It is a further object of the present invention to provide a method for manufacturing a flexible sealed radioactive film for medical treatments.

It is another object of the invention to provide radioactive sources for medical treatments which can be stacked upon one another or pieced to one another to provide a desired custom made radiation dosage to a specific area of treatment.

The foregoing objects and others are achieved by providing a flexible sealed radioactive film comprising a radioactive material on or in a flexible thin film carrier body, wherein tho radioactive carrier body is sealed in a flexible envelope. A number of flexible sealed radioactive film units can be provided in the form of a perforated strip wherein any number of flexible sealed film units can be easily removed from the perforated strip and applied to the site of treatment.

BRIEF DESCRIPTION OF THE DRAWINGS

For a better understanding of the structure, advantages and further features of the flexible sealed radioactive film of the present invention, reference is made to the accompanying drawings, wherein.

DETAILED DESCRIPTION OF THE INVENTION

Figure 1:
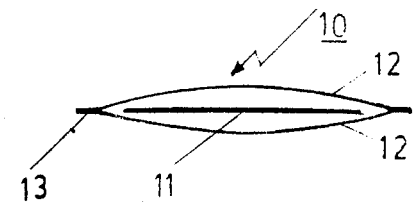
FIG. 1 is a partially schematic cross-sectional view showing a preferred embodiment of the structure of the flexible sealed radioactive film of the present invention
Figure 2:
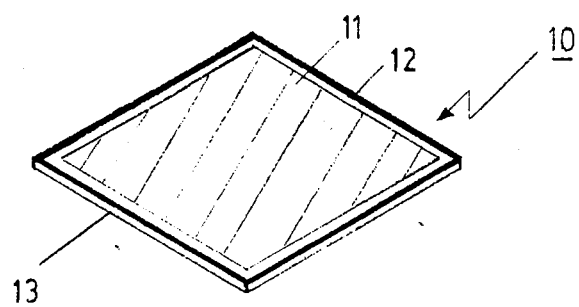
FIG. 2 is a partially schematic isometric view of a preferred embodiment of the flexible sealed radioactive film of the present invention.
Figure 3:
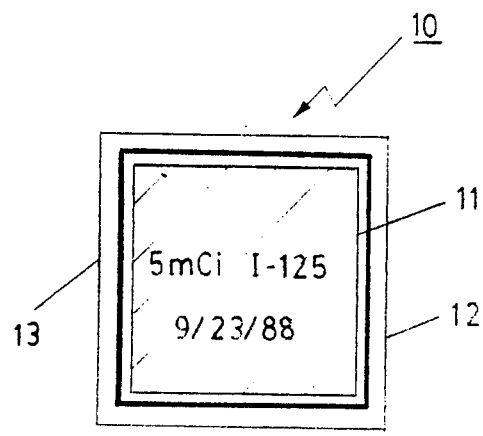
FIG. 3 is a partially schematic plan view of the flexible sealed radioactive film of the present invention, similar to that illustrated in FIGS. 1 and 2.

A preferred embodiment of the flexible sealed radioactive film of the present invention is illustrated in FIGS. 1-3. A flexible sealed radioactive film 10 of the present invention comprises a substantially two-dimensional flexible carrier film 11 enclosed in a substantially two-dimensional flexible sealed envelope 12. The flexible carrier film 11 is coated or impregnated with a radioactive material.

The radioactive material provides the source of radiation in the invention. A number of known radioactive materials may be used as the source of radiation. These known sources of radiation include $^{125}I$, $^{32}P$, $^{103}Pd$, $^{131}Cs$, $^{134}Cs$, $^{137}Cs$, $^{111}Ag$, $^{235}U$, $^{198}Au$ and $^{14}C$, as well as isotopes of rubidium, calcium, barium, scandium, titanium, chromium, iron, cobalt, nickel, copper, zinc, yttrium, zirconium, indium, cadmium, the rare earths, mercury, lead, americium and neptunium. Of these known sources, $^{125}$I and $^{32}$P are most preferably used in the present invention due to their preferred properties for medical radiation treatments.

The radioactive material may also be in the form of a radio-labeled polyamino acid. Radio-labeled polyamino acids can be formed from polyamino acids which are capable of chemically binding radioactive substituents. The radioactive substituent to be chemically bound by the polyamino acid is preferably employed through the use of $^{125}$I sodium iodide with a specific activity of about 17.4 Ci/mg. In particular, an aromatic polyamino acid such as polytyrosine can be labeled with $^{125}$I at the 3' and 4' positions of the aromatic ring of the tyrosine molecules of the polypeptide chain.

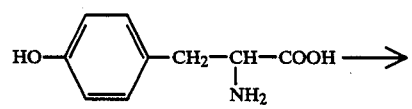

Tyrosine

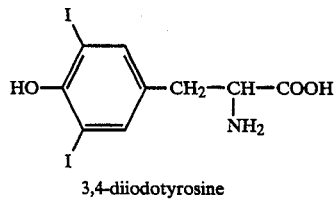

3,4-diiodotyrosine

Theoretically, each tyrosine residue is capable of taking up two atoms of iodine. A polytyrosine of molecular weight of about 100,000 has about 553 tyrosine residues. Thus, one mole of polytyrosine can bind about 1,105 iodine atoms. In gravimetric terms, each milligram of polytyrosine can thus bind about 8–10 Ci of $^{125}$I. Therefore, it is evident that a small quantity of polytyrosine is capable of tightly binding an enormous amount of $^{125}$I.

Preferably, poly-D-tyrosine labeled with $^{125}$I is employed as the radioactive material. The advantages of utilizing the D isomer of polytyrosine are particularly evident should polytyrosine enter the body. Free $^{125}$I is known to be readily taken up by the body in the thyroid gland. Poly-D-tyrosine, being the unnatural isomer for higher organisms including man, cannot be broken down by the body. Thus, the $^{125}$I will remain effectively bound to the poly-D-tyrosine, and not be taken up by the thyroid gland. It is well known that free iodine, including the radioactive form thereof, has a great tendency to accumulate in the thyroid when iodine is free to move within the body.

It is evident that polyamino acids other than polytyrosine, as well as radioisotopes other than $^{125}$I, may be used in the present invention. A useful radioisotope must be capable of binding with available sites on the polyamino acid. For example, $^{14}$C may be incorporated into the epsilon amino group of lysine by reductive methylation with $^{14}$C formaldehyde and sodium borohydride to give a covalently bound $^{14}$C label on the lysine molecule. Other radioisotopes such as $^{32}$P can also be incorporated into polynucleotides. Some polynucleotides which can be labeled with $^{32}$P include polyadenylic acid, polyguanylic acid, polythymidylic acid, polycytidylic acid and the like.

It will be appreciated that other large molecules including polymers can be selected having a varying number of available binding sites, thereby permitting the total radioactivity of the final radioactive source to vary.

The radioactive material of the present invention is coated onto or dispersed in a flexible carrier film. A thin coating can be easily coated uniformly onto or dispersed in the flexible carrier film giving a desired amount of radioactivity per unit area of the flexible carrier film. Depending upon the amount of radiation exposure desired from the film product, more or less radioactive material can be incorporated onto the flexible carrier film. Typically, the flexible carrier film is made of a material which can selectively trap the radioactive material while impurities are not retained.

In a preferred embodiment, a membrane filter having uniform pore size is utilized as the flexible carrier film. The membrane filter is preferably coated with a radio-labeled polyamino acid. The membrane filter is chosen such that when labeled polyamino acid in solution is passed through the membrane filter, the polyamino acid is trapped while impurities are allowed to pass therethrough. The pore size in the membrane filter will typically range from about 0.1 microns to about 1 micron so that compounds of molecular weight larger than about 10,000 are trapped while impurities having a molecular weight less than about 10,000 are allowed to pass. In other words, a membrane filter is selected having a pore size which will not allow the radioactively labeled polymer molecules of molecular weight more than 10,000 to pass, but will allow smaller molecules such as free $^{125}$I sodium iodide or other reactants to pass uninhibited. For example, when preparing radio-labeled polyamino acid in solution, the solution may contain labeled polyamino acid as well as unreacted free radioisotopes and other reactants. By selecting a membrane filter having a pore size which selectively retains the labeled polyamino acid, the unreacted free radioisotopes and other reactants can be removed by thoroughly washing the filter with water The radio-labeled polyamino acid will be selectively retained on the filter. Therefore, the particular labeled polyamino acid can be uniformly coated on the filter as a thin coating.

The pore size of the filter utilized will depend on the molecular weight or size of the labeled polyamino acid. Typically, a pore size of about 0.45 microns is adequate to trap the polyamino acid while allowing impurities to pass. Other suitable pore sizes can range from about 0.1 microns to about 1 micron. Examples of such materials for the membrane filter include polyvinyl chloride, polytetrafluoroethylene, polysulfones, cellulose esters, nylon, Dacron, polypropylene and the like.

The flexible carrier film may contain radioactive absorbing materials such as activated carbon and the like. For example, radioactive $^{125}$I in solution is readily absorbed by activated carbon powder. Activated carbon powder can be impregnated into the flexible carrier film and then allowed to soak in a solution of $^{125}$I. The flexible impregnated carrier film is then removed from the solution and allowed to dry, thereby leaving radioactive coated carbon dispersed in the flexible carrier film. Similar methods with other absorbing materials may also be employed.

Other useful radioactive absorbing materials include activated charcoal, ion exchange resins such as sulfonated polystyrene resins, methylene-sulfonic phenolic resins, phosphoric polystyrene resins, polystyrene resins containing quaternary ammonium groups, pyridinium polystyrene resins, epoxy-polyamine resins containing tertiary and quaternary ammonium groups, iminodiacetic polystyrene resins, and polystyrene resins containing polyamine groups. Such radioactive absorbing materials must be in a form so the flexibility of the resulting flexible carrier film is maintained when the absorbing materials are contained therein.

The flexible carrier film can range from about 20 to about 1000 microns thick, and is typically about 125 microns thick, allowing it to be easily cut into any desired dimension or shape depending on the particular application. The most typical shape is rectangular, and having dimensions ranging from about 2 mm×2 mm to about 100 mm×100 mm. However, it is readily apparent that the flexible carrier film can be cut into any imaginable shape depending on its application.

After the flexible carrier film is coated with the radioactive material, the coated flexible carrier film is sealed in an envelope of a polymer material such as polytetrafluoroethylene. Other materials which can be used for the envelope include polyethylene, cellulose esters, polysulfones, and the like. The envelope 12 is sealed around an outer edge 13, thereby preventing any leakage of the radioactive material. The sealing of the envelope can be accomplished by adhesives, heat sealing and other known sealing techniques.

Like the flexible carrier film, the envelope can be constructed in a variety of shapes, and most preferably, in the same shape as the substrate, but slightly larger so as to allow the sealed edge 13 to be formed. The thickness of the walls of the envelope can range from about 50 microns to about 1000 microns, as long as a suitable thickness is maintained to prevent the envelope from rupturing. Rupturing of the envelope may lead to undesirable leakage of the radioactive material which may in turn affect healthy tissue of the patient or medical personnel handling the flexible sealed radioactive films.

The flexible carrier film can be enclosed by means other than by a sealed envelope. For example, the flexible carrier film can be sealed by spraying on a coating of sealing material such as cyanoacrylate. Alternatively, the flexible carrier film can be sealed by one or two strips of adhesive tape. When an adhesive tape is used, the flexible carrier film is positioned on the adhesive side of one piece of adhesive tape and then the flexible film is covered by either another piece of adhesive tape or a material which is the same as the non-adhesive portion of the tape. A seal is thus formed around the entirety of the flexible carrier film. Alternatively, pieces of material having heat sealable margin portions may be used in place of the tape.

Advantageously, a double-sealed package can be obtained by enclosing the above spray-coated or tape coated flexible carrier film in a sealed envelope. Such double-sealed packages provide extra protection against undesirable leakage.

The flexible sealed radioactive film 10 of the present invention can be applied directly to the site of therapy and held in position by adhesive tape, for example. In this embodiment the flexible sealed radioactive film is placed at the treatment site and adhesive tape is applied to hold the flexible sealed radioactive film in position, much like a bandage. Advantageously, an adhesive may be incorporated directly on at least one side of the flexible sealed radioactive film to permit easy application to the treatment site. If the flexible sealed radioactive film is provided with adhesive on its outer surface, the films can adhere to one another as well as to the site where the film is applied. The adhesive can further be provided with a protective covering. When the flexible sealed radioactive film is ready for use, the covering is peeled from the film, thereby exposing the adhesive. Thus, the flexible sealed radioactive film of the present invention obviates the need for complicated and expensive application techniques.

Suitable adhesives which can be utilized in the present invention may be selected from one of the well-known skin contact adhesives such as those disclosed in U.S. Pat. Nos. 3,189,581; 3,218,357; 3,325,459 and 4,112,213. These adhesives are generally copolymers of 2-ethylhexyl acrylate and vinyl acetate in ratios of about 60-70 parts of the acrylate and 30-40 parts of the vinyl acetate. The polymers may also contain small amounts of N-tertiary butylacrylamide as a third monomer and a crosslinking agent. Water-based and hot-melt adhesives may also be employed.

Figure 4:
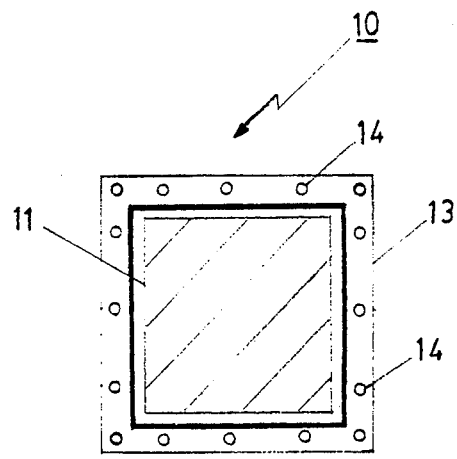
FIG. 4 is a partially schematic plan view of an embodiment of the flexible sealed radioactive film of the present invention.

The flexible sealed radioactive film can also be held in position by suturing. It is important that the suturing does not rupture the sealed portion of the film and thus cause any of the radioactive material to escape. Therefore, the suturing is preferably made along the sealed edge 13 of the film 10. In this respect, the edge 13 can be provided with suture holes 14 as shown in FIG. 4. The suture holes 14 allow a surgeon to readily suture the flexible sealed radioactive film to the therapy site. The holes 14 not only provide a convenient method for suturing the film to the patient, but also ensure that the surgeon does not puncture the flexible sealed radioactive film in an area which would allow radioactive material to escape from the envelope. The suture holes can be formed by puncturing and other known hole forming techniques.

More than one flexible sealed radioactive film can be applied to the therapy site to increase the radiation dosage and/or increase the area being treated. By using any number of flexible radioactive film units, a surgeon can readily adapt the units to provide the desired dosage in the desired area to be treated. Thus, a kind of patchwork pattern can be custom made by the surgeon to fit the particular application.

The flexible sealed radioactive film of the present invention can thus be readily adapted for both external and internal applications. For example, the flexible sealed radioactive film can be applied to the walls of cavities remaining after the removal of a tumor and held in place by suturing. Any number of sealed films can be applied around the cavity to cover the area being treated and held in place accordingly. Likewise, any number of sealed films can be applied externally and held in place by bandaging, adhesives or the like.

In some applications, it may be desireable to allow radiation to pass from only one side of the film. Such a situation arises when the sealed film is placed between an area of healthy tissue and tissue in need of treatment. In such a case, one side of the film may be provided with a shield on the side intended to face healthy tissue, which prevents radiation from passing therethrough. The provision of a shield can also be utilized for external applications to provide protection for personnel in the vicinity of the patient being treated. The shield can be adhesively attached to the side of the flexible sealed radioactive film and may be provided within the flexible sealed radioactive film or within sealed envelopes if more than one sealed envelope is used. Shielding materials can be selected from any number of known materials for the purpose. These materials include tin, silver, platinum, gold, tungsten, stainless steel, lead, brass, copper and alloys thereof. For isotopes of $^{125}$I and $^{32}$P, tin foil is preferably utilized as a shield.

Figure 5:
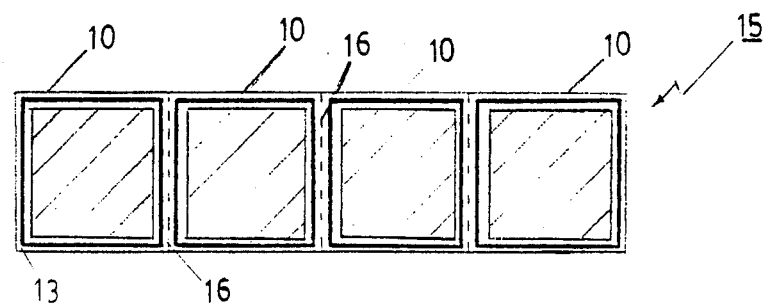
FIG. 5 is a partially schematic plan view of an embodiment of the present invention of a number of flexible sealed film units in the form of a perforated strip of units of flexible sealed radioactive film.

An advantageous form of dispensing the flexible sealed radioactive film units of the present invention is illustrated in FIG. 5. FIG. 5 shows a number of flexible sealed radioactive film units 10 in the form of a strip 15. Each flexible sealed radioactive film unit 10 of the strip 15 is provided with a sealed edge 13. One or more units can be easily cut or torn from the strip 15 along perforations 16 provided between each corresponding unit 10. These perforations can be formed by any known perforation forming means. The perforations 16 ensure that each unit is separated within the sealed edge 13, thereby preventing undesirable rupturing of the flexible sealed radioactive film. When dispensing the flexible sealed radioactive film in the form of a strip, a surgeon can easily remove the units as they are needed.

It will be appreciated that the flexible sealed radioactive films of the present invention may be marked with indicia to indicate to personnel information about the material they are handling. For instance, the flexible sealed radioactive films can be marked to indicate the particular dosage of each flexible sealed radioactive film, type of radioactive material, the size of the film, type of isotope, date of calibration, or to communicate any other desired information relating to the radioactive film. These markings can be applied by known marking and printing techniques. Such markings could not be employed on other radioactive treatment sources, such as seeds, due to their small size and shape.

From the foregoing description of the flexible sealed radioactive film and strip and methods of making same of the present invention, it is apparent that many advantages stem therefrom, including ease of application to irregular treatment sites, ease of variation of radioactive dose, ease of marking, and the like.

The present invention is further illustrated by reference to the following example.

EXAMPLE

A solution (about 50 µl) of poly-D-tyrosine (Sigma Chemical Co., St. Louis, Mo.), approximately 2 mg/ml in 0.1M NaOH is placed in a Beckman microfuge tube to which about 50 µl of 1N HCl is added followed by the addition of about 50 µl of 0.2M borate buffer, pH 7.9. Iodination is carried out by adding about 2 µl of career-free $^{125}$I-sodium iodide (Syntechem Co., N.Y., N.Y., 0.5 Ci/ml) followed by the addition of about 50 µl of chloroamine-T solution, 30 mg/ml H$_2$O, (Eastman Kodak Ltd., Rochester, N.Y.). The mixture is allowed to react for 30 seconds when about 50 µl of sodium metabisulfite 10 mg/ml H$_2$0 (Fisher Scientific Co., Columbia, Md.) is added to stop the reaction. The final reaction mixture is filtered under reduced pressure through a hydrophilic Durapore filter about 175 microns thick, being about 0.45 micron pore size and about 1 cm in diameter; (Millipore Corporation, Bedford, Mass.) and the filter is washed thoroughly with water to remove unreacted free $^{125}$I sodium iodide and all other reactants. The $^{125}$I labeled polytyrosine does not pass completely through the pores of the filter and is selectively retained on the filter. Thus, $^{125}$I is uniformly coated on the filter as a thin film giving a desired amount of radioactivity. The filter is air dried and completely sealed in a double envelope of polytetrafluoroethylene to produce the flexible sealed radioactive film. This can be directly applied to the site of therapy with an adhesive tape. This procedure can be scaled up to any level depending upon the required final $^{125}$I radioactivity in the strip.

While the foregoing descriptions of the advantageous radioactive sources and methods of making the same of the present invention have described various embodiments thereof, it will be appreciated by those skilled in the art that various modifications can be made in such sources and methods without departing from the scope and spirit of the invention as stated in the following claims.

What is claimed is:

1. A flexible sealed radioactive film for medical treatments including implantation within a living body, comprising:
   a substantially flat, flexible carrier film;
   a radioactive material in or on said flexible carrier film; and
   a substantially flat, flexible envelope having the flexible carrier film sealed therein.

2. The flexible sealed radioactive film of claim 1, wherein, said carrier film comprises a material selected from the group consisting of polyvinyl chloride, polytetrafluoroethylene, cellulose esters and polysulfones.

3. The flexible sealed radioactive film of claim 1, wherein said carrier film is a membrane filter.

4. The flexible sealed radioactive film of claim 3, wherein said membrane- filter has a pore size sufficiently small to trap said radioactive material thereon.

5. The flexible sealed radioactive film of claim 4, wherein said pore size ranges from about 0.1 microns to about 1.0 microns.

6. The flexible sealed radioactive film of claim 5, wherein said pore size is about 0.45 microns.

7. The flexible sealed radioactive film of claim 1, wherein said carrier film is from about 20 to about 1000 microns thick.

8. The flexible sealed radioactive film of claim 7, wherein said carrier film is about 125 microns thick.

9. The flexible sealed radioactive film of claim 1, wherein said carrier film has dimensions ranging from about 2 mm×2 mm to about 100 mm×100 mm.

10. The flexible sealed radioactive film of claim 1, wherein said carrier film contains a radioactive absorbing material.

11. The flexible sealed radioactive film of claim 10, wherein said radioactive absorbing material is selected from the group consisting of activated carbon, charcoal, sulfonated polystyrene resins, methylene-sulfonic phenolic resins, phosphoric polystyrene resins, polystyrene resins containing quaternary ammonium groups, pyridinium polystyrene resins, epoxy-polyamine resins containing tertiary and quaternary ammonium groups, iminodiacetic polystyrene resins, and polystyrene resins containing polyamine groups.

12. The flexible sealed radioactive film of claim 1, wherein said radioactive material is a radio-labeled polyamino acid.

13. The flexible sealed radioactive film of claim 12, wherein said radio-labeled polyamino acid is radio-labeled polytyrosine .

14. The flexible sealed radioactive film of claim 12, wherein said polyamino acid is labeled with $^{125}$I or $^{14}$C.

15. The flexible sealed radioactive film of claim 13, wherein said radio-labeled polytyrosine is poly-D-tyrosine.

16. The flexible sealed radioactive film of claim 1, wherein said radioactive material is a radio-labeled polynucleotide.

17. The flexible sealed radioactive film of claim 16, wherein said polynucleotide is labeled with $^{32}P$.

18. The flexible sealed radioactive film of claim 1, wherein said radioactive material is a molecule having a molecular weight greater than 10,000 and having a varying number of binding sites for radioactive substituents.

19. The flexible sealed radioactive film of claim 1, wherein said radioactive material is selected from the group consisting of $^{125}I$, $^{103}Pd$, $^{131}Cs$, $^{134}Cs$, $^{137}Cs$, $^{111}Ag$, $^{235}U$, $^{198}Au$, $^{32}P$ and $^{14}C$, and isotopes of rubidium, calcium, barium, scandium, titanium, chromium, manganese, iron, cobalt, nickel, copper, zinc, yttrium, zirconium, indium, cadmium, the rare earths, mercury, lead, americium and neptunium.

20. The flexible sealed radioactive film of claim 1, wherein said radioactive material is $^{125}I$.

21. The flexible sealed radioactive film of claim 1, wherein said radioactive material is $^{32}P$.

22. The flexible sealed radioactive film of claim 1, wherein said envelope is made of a material selected from the group consisting of polytetrafluoroethylene, polyethylene, cellulose esters and polysulfones.

23. The flexible sealed radioactive film of claim 1 wherein said envelope has a wall thickness in the range of about 50 microns to about 1000 microns.

24. The flexible sealed radioactive film of claim 1, further comprising a sealed edge around the outer periphery of said envelope.

25. The flexible sealed radioactive film of claim 24, wherein said edge includes suture holes.

26. The flexible sealed radioactive film of claim 1, wherein an adhesive layer is provided on at least one side of said envelope.

27. The flexible sealed radioactive film of claim 26, further comprising a protective, peelable covering for said adhesive layer.

28. The flexible sealed radioactive film of claim 1, wherein two or more sealed films are integrally held together at edges thereof to form a strip.

29. The flexible sealed radioactive film of claim 28, wherein said strip includes perforations between each corresponding sealed film.

30. The flexible sealed radioactive film of claim 1, wherein one side of said envelope is provided with a radiation shielding material.

31. The flexible sealed radioactive film of claim 30, wherein said radiation shielding material is selected from the group consisting of tin, silver, lead, gold, tungsten, platinum, stainless steel, brass, copper and alloys thereof.

32. The flexible sealed radioactive film of claim 30, wherein said shielding material is tin foil.

33. The flexible sealed radioactive film of claim 1, wherein said flexible carrier film is coated with a sealing material to form said envelope.

34. The flexible sealed radioactive film of claim 33, wherein said sealing material is cyanoacrylate.

35. The flexible sealed radioactive film of claim 1, further comprising a second substantial two-dimensional flexible envelope having the flexible sealed radioactive film sealed therein.

36. The flexible sealed radioactive film of claim 1, wherein said envelope comprises tape.

37. The flexible sealed radioactive film of claim 1, further comprising marking indicia on said envelope.

* * * * *